[12] United States Patent  
Masters

[10] Patent No.: US 6,585,656 B2  
[45] Date of Patent: *Jul. 1, 2003

[54] CATHETER WITH MULTIPLE TRANSDUCERS

[75] Inventor: Donald Masters, Sunnyvale, CA (US)

[73] Assignee: Scimed Life Systems, Inc., Maple Grove, MN (US)

[*] Notice: Subject to any disclaimer, the term of this patent is extended or adjusted under 35 U.S.C. 154(b) by 0 days.

This patent is subject to a terminal disclaimer.

[21] Appl. No.: 10/072,186

[22] Filed: Feb. 5, 2002

[65] Prior Publication Data

US 2002/0072669 A1 Jun. 13, 2002

Related U.S. Application Data

[63] Continuation of application No. 09/499,591, filed on Feb. 7, 2000, now Pat. No. 6,361,500.

[51] Int. Cl.[7] .............................................. A61B 8/14  
[52] U.S. Cl. ..................................................... 600/466  
[58] Field of Search ................................ 600/443–447, 600/459, 462, 463, 466, 467; 73/625, 633, 626; 607/97

[56] References Cited

U.S. PATENT DOCUMENTS

| | | | | |
|---|---|---|---|---|
| 3,542,014 A | 11/1970 | Peronneau | | 128/2 |
| 3,779,234 A | 12/1973 | Eggleton et al. | | 128/2 |
| 3,817,089 A | 6/1974 | Eggleton et al. | | 73/67.8 S |
| 4,671,295 A | 6/1987 | Abrams et al. | | 128/663 |
| 4,757,821 A | 7/1988 | Snyder | | 128/660 |
| 4,841,977 A | 6/1989 | Griffith et al. | | 128/660.03 |
| 4,850,363 A | 7/1989 | Yanagawa | | 128/660.09 |
| 5,078,148 A | 1/1992 | Nassi et al. | | 128/661.09 |
| 5,400,788 A | 3/1995 | Dias et al. | | 128/662.03 |
| 5,406,951 A | 4/1995 | ten Hoff et al. | | 128/662.06 |
| 5,471,988 A | 12/1995 | Fujio et al. | | 128/660.03 |
| 5,479,928 A | 1/1996 | Cathignol et al. | | 128/662.06 |
| 5,620,479 A | 4/1997 | Diederich | | 607/97 |
| 5,655,537 A | 8/1997 | Crowley | | 128/662.06 |
| 5,704,361 A | 1/1998 | Seward et al. | | 128/662.06 |
| 5,720,287 A | 2/1998 | Chapelon et al. | | 128/660.03 |
| 5,724,978 A | 3/1998 | Tenhoff | | 128/662.06 |
| 5,848,969 A | 12/1998 | Panescu et al. | | 600/462 |
| 6,102,865 A | 8/2000 | Hossack et al. | | 600/459 |
| 6,131,458 A | 10/2000 | Langdon et al. | | 73/627 |
| 6,224,556 B1 | 5/2001 | Schwartz et al. | | 600/447 |
| 6,361,500 B1 * | 3/2002 | Masters | | 600/466 |

* cited by examiner

Primary Examiner—Marvin M. Lateef  
Assistant Examiner—Ali M. Imam  
(74) Attorney, Agent, or Firm—Orrick, Herrington & Sutcliffe LLP

(57) ABSTRACT

A diagnostic and/or therapeutic catheter having a plurality of ultrasound transducers. In a first embodiment, the center frequencies of the second and third transducers may be substantially equal to a fundamental harmonic and a second harmonic, respectively, of ultrasound waves created by the first transducer. In second embodiment, the second transducer transmits waves with a center frequency substantially equal to the center frequency of the first transducer. In third embodiment, the second transducer has a center frequency that differs from the center frequency of the first transducer and the center frequency of the third transducer may be substantially equal to a difference between the fundamental harmonic of the ultrasound waves transmitted by the first transducer and a fundamental harmonic of ultrasound waves produced by the second transducer.

72 Claims, 4 Drawing Sheets

CATHETER WITH MULTIPLE TRANSDUCERS

CROSS-REFERENCE TO RELATED APPLICATIONS

This application is a continuation of co-pending patent application, U.S. Ser. No. 09/499,591, filed Feb. 7, 2000. The priority of this application is expressly claimed and its disclosure is hereby incorporated by reference in its entirety.

BACKGROUND OF THE INVENTION

1. Field of the Invention

The present invention relates generally to medical ultrasound systems and, more particularly, to a diagnostic and/or therapeutic catheter providing a plurality of ultrasound transducers within a distal end of a drive shaft.

2. Background of the Invention

Intraluminal, intracavity, intravascular, and intracardiac diagnosis and treatment of medical conditions utilizing minimally invasive procedures is an effective tool in many areas of medical practice. These procedures typically are performed using imaging and treatment catheters that may be inserted into either an opening in a patient's body or percutaneously into an accessible vessel, such as the femoral artery, of the vascular system at a site remote from a region of the patient's body to be diagnosed and/or treated. The catheter then may be advanced, for example, through the vessels of the vascular system to the region of the patient's body to be diagnosed and/or treated, such as a vessel or an organ. The catheter may be equipped with an imaging device, typically an ultrasound imaging device, which may be used to locate and diagnose a diseased portion of the patient's body, such as a stenosed region of an artery. The catheter may alternatively include an ultrasound transducer for therapeutically treating or, if desired, disintegrating the diseased portion of the patient's body.

Intravascular imaging systems having ultrasound imaging capabilities generally are known. For example, U.S. Pat. No. 4,951,677, issued to Crowley, the disclosure of which is incorporated herein by reference, describes an intravascular ultrasound imaging system. An ultrasound imaging system typically contains some type of control system, a drive shaft, and a transducer assembly including an ultrasound transducer. The transducer assembly includes a transducer element and is coupled to the control system by the drive shaft. The drive shaft typically permits communication between the control system and the ultrasound transducer.

In operation, the drive shaft and the transducer assembly are inserted, usually within a catheter, into a patient's body and may be positioned near a remote region. To provide diagnostic scans of the remote region within, for example, a coronary blood vessel, the ultrasound transducer may be positioned near or within the remote region of the patient's body. Diagnostic scans are created when the control system alternately excites and allows sensing by the ultrasound transducer. The control system may direct the ultrasound transducer toward an area of interest within the remote region. When the ultrasound transducer is excited, the ultrasound transducer creates ultrasound waves in the bodily fluids surrounding the ultrasound transducer. The ultrasound waves then propagate through the fluids within the patent's body and ultimately reach the area of interest, forming reflected ultrasound waves. The reflected ultrasound waves then return through the fluids within the patient's body to the ultrasound transducer, inducing electrical signals within the ultrasound transducer. The control system then may collect the induced electrical signals and may reposition the ultrasound transducer to an adjacent area within the remote region of the patient's body, again exciting and sensing the ultrasound transducer. This process may continue until the remote region has been examined sufficiently and a series of induced signals has been collected. The control system then may process the series of induced signals to derive a diagnostic scan and may display a complete image of the diagnostic scan.

Ultrasound waves may also be used to therapeutically treat or, if desired, disintegrate a diseased portion of a patient's body. Intraluminal systems and catheters for providing ultrasound therapy are generally known. For example, U.S. Pat. No. 5,471,988, issue to Fujio et al., the disclosure of which is incorporated herein by reference, describes such an intraluminal ultrasound therapy system. Like the ultrasound imaging system, an ultrasound therapy system generally includes a control system and a transducer assembly, each communicating with a drive shaft. However, whereas ultrasound imaging systems typically use low intensity ultrasound waves, ultrasound therapy systems may require higher intensity ultrasound waves than the ultrasound waves used for imaging or diagnosis.

As in the ultrasound imaging system, the drive shaft and the transducer assembly of the ultrasound therapy system are inserted, usually within a catheter, into a patient's body and may be positioned near a remote region to be treated. When the control system excites the transducer assembly directed toward the area of interest, high intensity ultrasound waves may propagate from the ultrasound transducer and toward the area of interest. When the ultrasound waves reach the area of interest, the ultrasound waves may cause the area of interest to begin to vibrate. This vibration may cause the area of interest to be therapeutically heated to relieve pain or become stimulated or relaxed. If the area of interest is undesired, ultrasound waves may be transmitted at a resonant or critical frequency of the area of interest; thereby, the area of interest may be disintegrated. The control system may continue to excite the ultrasound transducer until the therapy has been completed.

Medical ultrasound systems for diagnosis and treatment, however, currently suffer from several deficiencies. First, the available resolution of the resultant diagnostic scans could be increased. Typical medical ultrasound systems utilize only a fundamental harmonic of the ultrasound waves generated by the ultrasound transducer. Additional resolution may be possible by also examining higher order harmonics of the ultrasound waves. Second, the size of the area of interest that may be treated by current medical ultrasound systems remains relatively small. Therapeutic catheters treat regions of a patient's body by directing intense ultrasound waves toward an area of interest in a patient's body. The intense ultrasound waves may induce the area of interest to vibrate, causing the area of interest to grow warm. A single transducer, however, may be focused only on a small region; thus, requiring individual regions of a large area of interest to be treated separately. Patients may benefit from having the entire area of interest treated simultaneously. Third, the ultrasound waves may suffer from attenuation during propagation through a patient's body. When the ultrasound transducers explore deeper into the patient's body, the ultrasound transducers may need to be reduced physically in size to fit within smaller regions, but, as the size of the ultrasound transducer decreases, the center frequency of the ultrasound transducer may increase. Since higher frequency ultrasound waves may be more subject to attenuation than lower frequency ultrasound waves, the depth of penetration of the higher frequency ultrasound waves may be limited.

In view of the foregoing, it is believed that a need exists for an improved catheter that overcomes the aforementioned obstacles and deficiencies of currently available diagnostic and therapeutic catheters.

SUMMARY OF THE INVENTION

The present invention is directed to a diagnostic and/or therapeutic catheter incorporating a drive shaft with a distal end having a plurality of ultrasound transducers for providing therapeutic treatment to or creating diagnostic images of an area of interest within a patient's body. The present invention provides the advantages of improved image resolution, enhanced ability to excite the area of interest, and increased penetration depth for diagnosis.

In one preferred form, a catheter in accordance with the present invention may comprise a drive shaft, a first ultrasound transducer for transmitting ultrasound waves, and a second ultrasound transducer and a third ultrasound transducer each for receiving ultrasound waves. The drive shaft may have a proximal end, rotatably communicating with an ultrasound imaging system, and a distal end. The first ultrasound transducer preferably is mounted on the distal end of the drive shaft and may have a preselected center frequency. The second ultrasound transducer may be mounted on the distal end of the drive shaft at a preselected distance from the first ultrasound transducer and may have a preselected center frequency substantially equal to a fundamental harmonic of ultrasound waves generated by the first ultrasound transducer. The third ultrasound transducer preferably is mounted on the distal end of the drive shaft at a preselected distance from the first ultrasound transducer and may have a preselected center frequency substantially equal to a second harmonic of the ultrasound waves generated by the first ultrasound transducer. The second ultrasound transducer and the third ultrasound transducer each preferably are directed to receive the fundamental harmonic and the second harmonic, respectively, of reflections of the ultrasound waves generated by the first ultrasound transducer.

In a second preferred embodiment, the second ultrasound transducer preferably transmits ultrasound waves and may have a center frequency substantially equal to the center frequency of the first ultrasound transducer. The first ultrasound transducer and the second ultrasound transducer each may be directed at a first end and a second end, respectively, of an area of interest, such as a tissue segment. When the first ultrasound transducer and the second ultrasound transducer are excited, the area of interest may be therapeutically treated or, if the area of interest is undesired, disintegrated.

In a third preferred embodiment, the second ultrasound transducer may be capable of transmitting and receiving ultrasound waves and preferably has a center frequency that differs from the center frequency of the first ultrasound transducer. The third ultrasound transducer preferably has a center frequency that is substantially equal to a difference between the fundamental harmonic of the ultrasound waves generated by the first ultrasound transducer and a fundamental harmonic of the ultrasound waves produced by the second ultrasound transducer. The first ultrasound transducer and the second ultrasound transducer may be directed such that the ultrasound waves of the first ultrasound transducer preferably converge with the ultrasound waves of the second ultrasound transducer, creating difference ultrasound waves. The ultrasound waves created by the second ultrasound transducer and the difference ultrasound waves each may be reflected by an area of interest and, thereafter, received by the second ultrasound transducer and the third ultrasound transducer, respectively.

It will be appreciated that a catheter having a plurality of ultrasound transducers in accordance with the present invention may increase the utility of diagnostic and/or therapeutic catheters. By analyzing both the fundamental harmonic and the second harmonic of the ultrasound waves of the first ultrasound transducer, more information about an area of interest may be available to the medical ultrasound system, and diagnostic images with higher resolutions may result. For example, soft tissues may reflect certain harmonics of the ultrasound waves better than other harmonics of the ultrasound waves; whereas, an accumulation of a harder material, such as plaque, on the tissues may provide stronger reflections of different harmonics of the ultrasound waves. Based upon the relative strengths of the reflected fundamental and second harmonics of the ultrasound waves, a physician may be able to determine the presence and type of material within an area of interest.

It may also be appreciated that a larger area of interest may be treated or, if the area of interest is undesirable, disintegrated with the catheter of the second embodiment because the first ultrasound transducer and the second ultrasound transducer both may be directed at the area of interest. Further, since the difference ultrasound waves of the third embodiment may have fundamental harmonic substantially equal to the difference between the fundamental harmonic of the ultrasound waves created by the first ultrasound transducer and the fundamental harmonic of the ultrasound waves produced by the second ultrasound transducer, the difference ultrasound waves may be lower in frequency than either the ultrasound waves of the first ultrasound transducer or the ultrasound waves of the second ultrasound transducer. While propagating through the patient's body, the difference ultrasound waves may be less subject to attenuation and may, therefore, experience a greater depth of penetration. Finally, it also will be appreciated that, through the use of catheters in accordance with the present invention, substantial savings in diagnostic and treatment costs may be passed on to patients required to undergo ultrasound diagnostic and/or treatment procedures, or to their insurers.

DETAILED DESCRIPTION OF THE PREFERRED EMBODIMENTS

Figure 1:
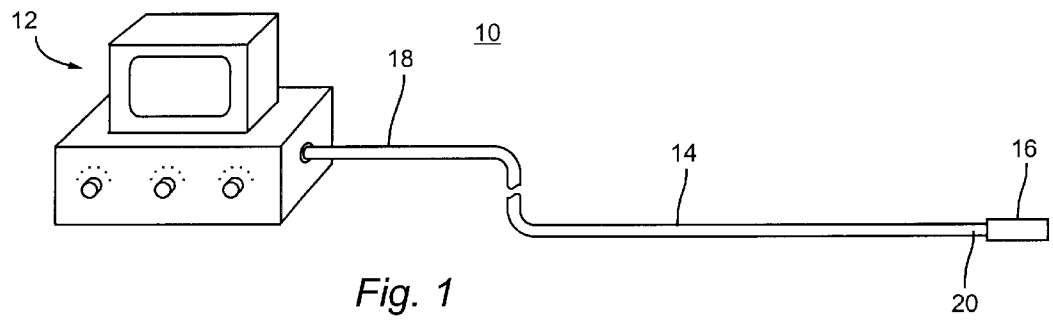
FIG. 1 is an illustration of a typical prior art medical ultrasound system.

Turning now to the drawings, FIG. 1 is an illustration of a typical medical ultrasound system 10. The medical ultrasound system 10 contains a control system 12, a drive shaft 14, and an ultrasound transducer assembly 16, having a center frequency (not shown). The drive shaft 14 may include a proximal end 18, communicating with the medical ultrasound system 10, and a distal end 20. The ultrasound transducer assembly 16 may communicate with the distal end 20 of the drive shaft 14 that may, in turn, couple the ultrasound transducer assembly 16 to the control system 12.

Figure 2A:
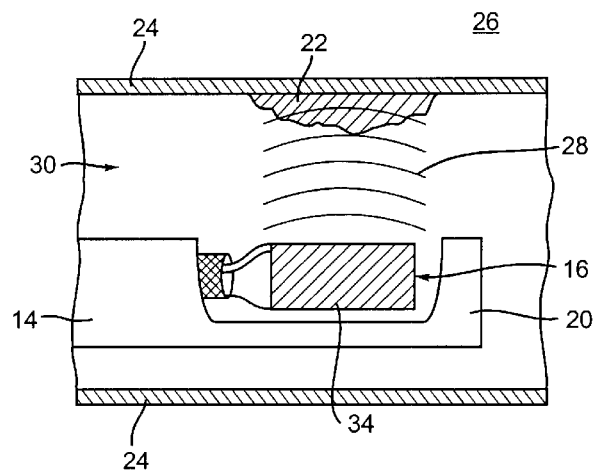
FIG. 2A is a detailed view of a prior art imaging catheter in a transmitting mode.
Figure 2B:
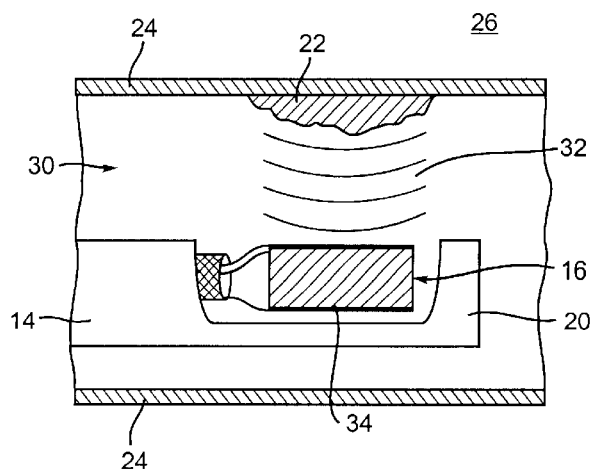
FIG. 2B is a detailed view of a prior art imaging catheter in a receiving mode.

As shown in FIG. 2A, to provide diagnostic scans of an area of interest 22 within, for example, a blood vessel 24, the ultrasound transducer assembly 16 may be positioned within a remote region 26 of a patient's body (not shown). Diagnostic scans are created when the control system 12 (shown in FIG. 1) alternately excites and allows sensing by the ultrasound transducer assembly 16. When the ultrasound transducer assembly 16 is excited, ultrasound waves 28, substantially comprising harmonics (not shown) of the center frequency of the ultrasound transducer assembly 16, are created in fluids 30 surrounding the ultrasound transducer assembly 16 within the patient's body. The ultrasound waves 28 then propagate through the fluids 30 within patent's body to the area of interest 22. A portion of the ultrasound waves 28 reflect from the area of interest 22, forming reflected ultrasound waves 32, as shown in FIG. 2B. The reflected ultrasound waves 32, substantially comprising harmonics (not shown) of the center frequency of the ultrasound transducer assembly 16, then return through the fluids 30 of the patient's body to the ultrasound transducer assembly 16. A fundamental harmonic (not shown) of the reflected ultrasound waves 32 induces electrical signals (not shown) within the ultrasound transducer assembly 16. The control system 12 (shown in FIG. 1) then may collect the induced electrical signals and may adjust the drive shaft 14 to direct the ultrasound transducer assembly 16 to an adjacent area (not shown) within the remote region 26 of the patient's body, again exciting and sensing the transducer element. This process may continue until the remote region 26 has been examined sufficiently and a series of induced signals has been collected. The control system 12 (shown in FIG. 1) then may process the series of induced signals to derive a diagnostic scan (not shown) and may display a complete image (not shown) of the diagnostic scan.

To create clear diagnostic scans, it is preferable that the ultrasound transducer assembly 16 be capable of receiving multiple harmonics of the reflected ultrasound waves 32. Lower frequency harmonics may be used to increase the resolution of the diagnostic scan, providing more information to a physician. Further, lower harmonics of the ultrasound waves generally are less subject to attenuation than is the fundamental harmonic of the ultrasound waves because higher frequencies generally are more subject to attenuation as they pass through the fluids 30 of the patent's body than are lower frequencies.

Figure 3:
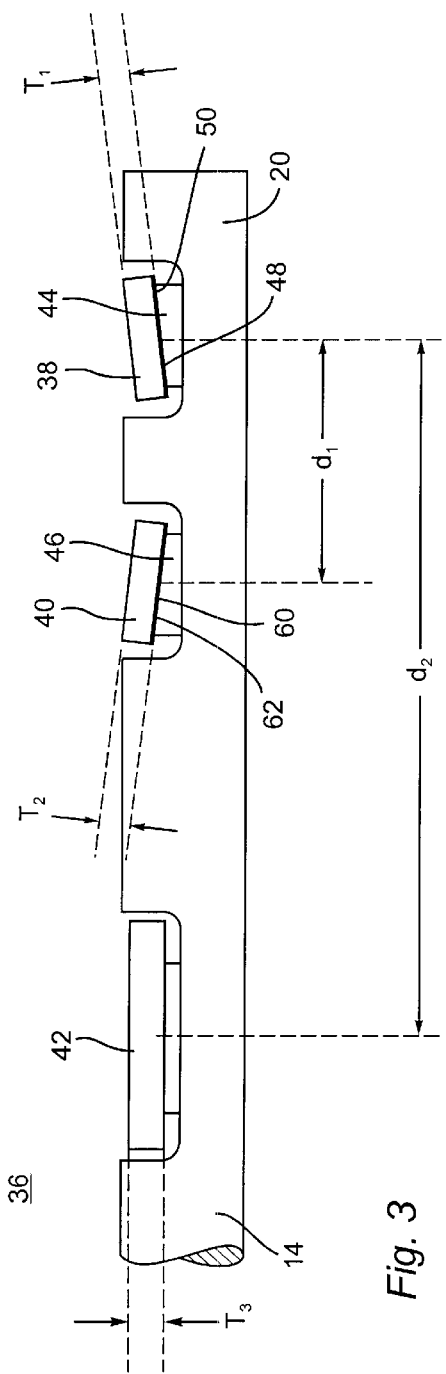
FIG. 3 is an illustration of one preferred embodiment of a catheter for medical ultrasound systems in accordance with the present invention.

This result may be achieved, according to one embodiment of the present invention, by employing a catheter 36, as shown in FIG. 3. The catheter 36 of the present invention preferably comprises a drive shaft 14, a first ultrasound transducer 38 for transmitting ultrasound waves, a second ultrasound transducer 40 for receiving ultrasound waves, and a third ultrasound transducer 42 for receiving ultrasound waves. The drive shaft 14 may have a proximal end (not shown), rotatably communicating with a medical ultrasound system (not shown), and a distal end 20.

The first ultrasound transducer 38 preferably is fixedly or adjustably mounted on the distal end 20 of the drive shaft 14, may electrically communicate with the medical ultrasound system, and may have a preselected center frequency (not shown). A first steering device 44 may be disposed between the first ultrasound transducer 38 and the distal end 20 to direct the first ultrasound transducer 38 toward an area of interest (not shown). The first steering device 44 preferably comprises a piezoelectric steering device or an electric-field device, but other types of steering devices also may be employed. The first ultrasound transducer 38 preferably has a substantially uniform thickness $T_1$ and preferably is substantially flat in shape.

The second ultrasound transducer 40 may be mounted on the distal end 20 of the drive shaft 14 at a preselected distance $d_1$ from the first ultrasound transducer 38 and may have a preselected center frequency (not shown). The preselected center frequency of the second ultrasound transducer 40 preferably is substantially equal to a fundamental harmonic (not shown) of the ultrasound waves generated by the first ultrasound transducer 38. The second ultrasound transducer 40 may have a substantially uniform thickness $T_2$, may be substantially flat in shape, and may be directed to receive ultrasound waves in a preselected plane (not shown). The second ultrasound transducer 40 may be fixedly or adjustably attached to the distal end 20 of the drive shaft 14. A second steering device 46 may be interposed between the second ultrasound transducer 40 and the distal end 20 of the drive shaft 14 to orient the second ultrasound transducer 40 toward an area of interest. Although other types of steering devices may be used, the second steering device 46 preferably comprises a piezoelectric steering device or an electric-field device.

The third ultrasound transducer 42 preferably is mounted on the distal end 20 of the drive shaft 14 at a preselected distance $d_2$ from the first ultrasound transducer 38 and may be fixedly mounted on the distal end 20 of the drive shaft 14. The third ultrasound transducer 42 may have a substantially uniform thickness $T_3$, may be substantially flat in shape, and may have a preselected center frequency (not shown) substantially equal to a second harmonic of the ultrasound waves produced by the first ultrasound transducer 38. The second ultrasound transducer 40 and the third ultrasound transducer 42 each preferably are directed to receive reflections (not shown) of the fundamental harmonic and the second harmonic, respectively, of the ultrasound waves generated by the first ultrasound transducer 38.

Figure 4:
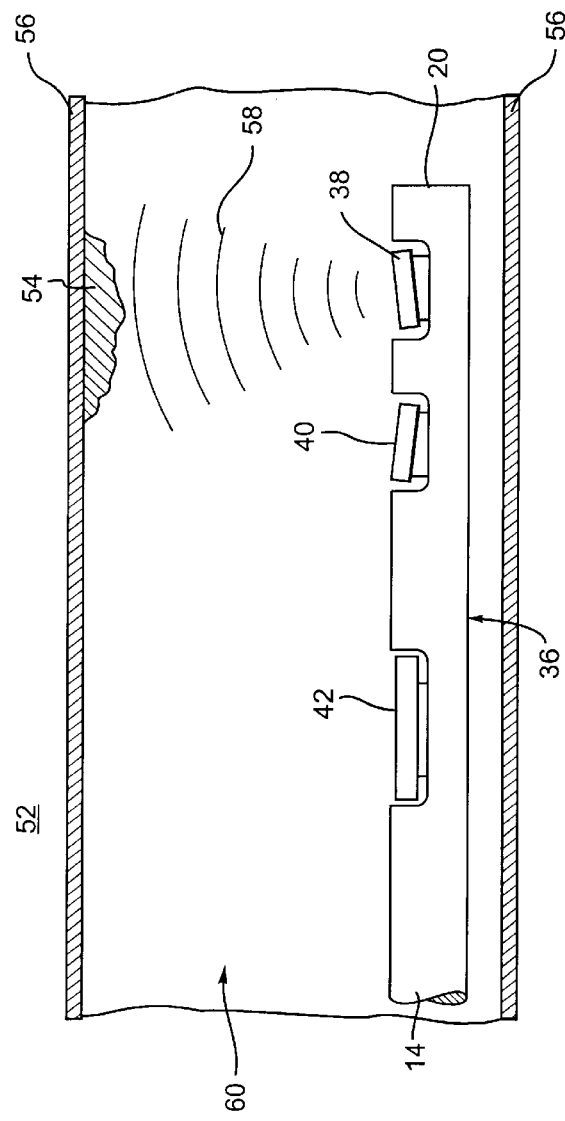
FIG. 4 is a detailed view of the catheter of FIG. 3 when operated in a transmitting mode.

As shown in FIG. 4, the catheter 36 of the present invention may be coupled to a control system 12 (shown in FIG. 1) of a medical ultrasound system 10 (shown in FIG. 1). The catheter 36 then may be positioned within a remote region 54 of a patient's body, providing diagnostic scans of an area of interest 52 on, for example, a blood vessel wall 56. The first ultrasound transducer 38 may be directed toward the area of interest 52 by either moving the catheter 36 within the blood vessel 56 or, preferably, by activating a first steering device 44. The second steering device 46 preferably may be used to direct the second ultrasound transducer 40 in the direction of the area of interest 52.

Figure 5:
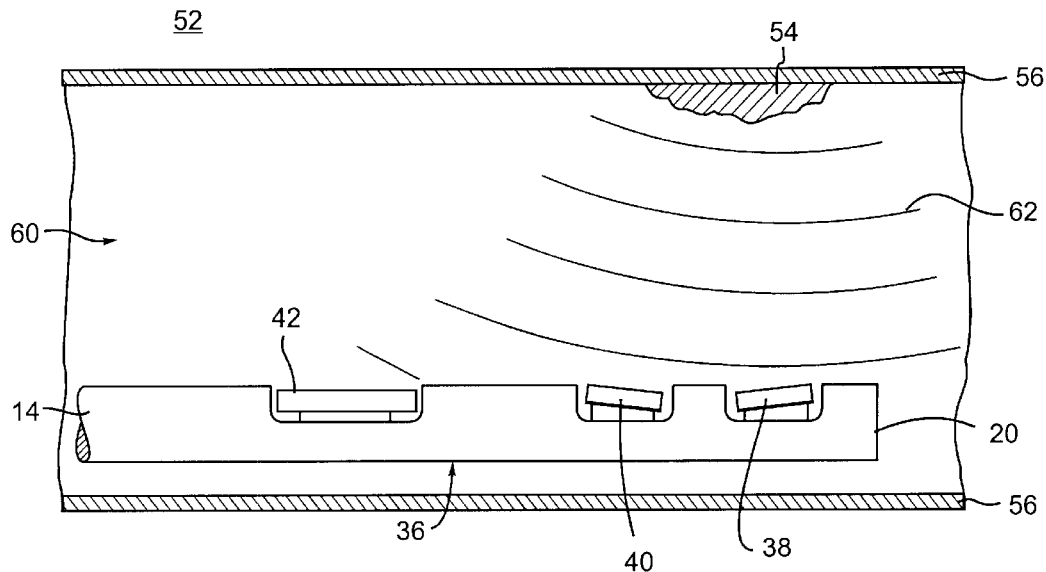
FIG. 5 is a detailed view of the catheter of FIG. 3 when operated in a receiving mode.

In operation, when the control system 12 excites the first ultrasound transducer 38, ultrasound waves 58, substantially comprising harmonics (not shown) of the center frequency of the first ultrasound transducer 38, may be produced in fluids 60 within the patient's body surrounding the first ultrasound transducer 38. The ultrasound waves 58 then may propagate through the fluids 60 within the patient's body from the first ultrasound transducer 38 to the area of interest 54. When the ultrasound waves 58 reach the area of interest 54, reflected ultrasound waves 62 may be formed, as shown in FIG. 5. The reflected ultrasound waves 62 may substantially comprise the harmonics of the center frequency of the first ultrasound transducer 38 and may return through the fluids 48 within the patient's body to the catheter 36.

Since the second ultrasound transducer 40 preferably has a center frequency substantially equal to a fundamental harmonic of ultrasound waves 58 generated by the first ultrasound transducer 38, the second ultrasound transducer 40 may be excited by a fundamental harmonic (not shown) of the reflected ultrasound waves 62, creating electrical signals (not shown). A second harmonic (not shown) of the reflected ultrasound waves 50 may induce electrical signals (not shown) within the third ultrasound transducer 42 because the third ultrasound transducer 42 preferably has a center frequency substantially equal to a second harmonic (not shown) of the ultrasound waves 58 of the first ultrasound transducer 38. The control system 12 (shown in FIG. 1) then may sense and process the induced electrical signals from the second ultrasound transducer 40 and the third ultrasound transducer 42 to develop a diagnostic scan (not shown) and display a complete image (not shown) of the diagnostic scan. Thus, the complete image may more accurately represent the area of interest 54 because the control system 12 may utilize information from both the fundamental and the second harmonics of the reflected ultrasound waves 50. The second harmonic of the reflected ultrasound waves 50 may be less subject to attenuation than the fundamental harmonic during propagation through the patient's body and also may provide additional resolution of the diagnostic scan.

Figure 6:
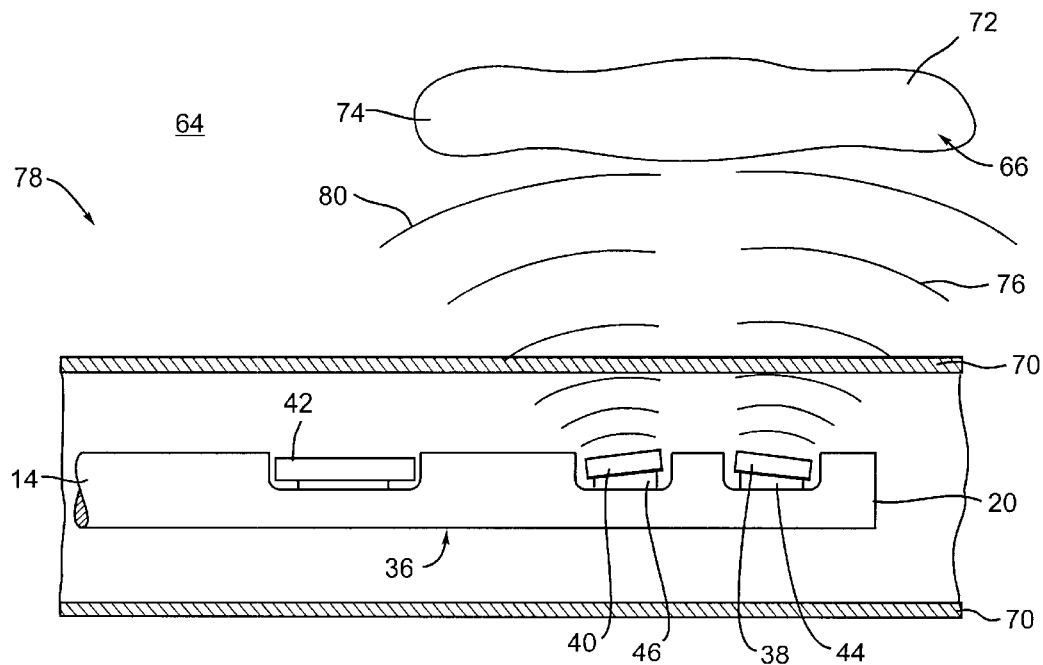
FIG. 6 is an illustration of a second preferred embodiment of a catheter in accordance with the present invention.

FIG. 6 depicts a second preferred embodiment of the catheter 36 of the present invention. The catheter 36 in the second embodiment preferably comprises a second ultrasound transducer 40 for transmitting ultrasound waves 80. The second ultrasound transducer 40 preferably has a preselected center frequency (not shown) substantially equal to the center frequency of the first ultrasound transducer 38 and may be directed to transmit ultrasound waves 80 that substantially diverge from ultrasound waves 76 generated by the first ultrasound transducer 38.

In operation, the catheter 36 may be positioned within, for example, a blood vessel 70 near a remote region 64 of a patient's body and provide treatment to a large area of interest 66 with a first end 72 and a second end 74. The first ultrasound transducer 38 may be directed toward the first end 72 of the large area of interest 66 by either moving the catheter 36 within the blood vessel 70 or, preferably, by activating the first steering device 44. The second steering device 46 preferably may be used to direct the second ultrasound transducer 40 at the second end 74 of the large area of interest 66. When the control system 12 (shown in FIG. 1) excites the first ultrasound transducer 38, first ultrasound waves 76 may be produced in fluids 78 within the patient's body surrounding the first ultrasound transducer 38. The first ultrasound waves 76 then may propagate through the fluids 60 within the patient's body from the first ultrasound transducer 38 to the first end 72 of the large area of interest 66. When the second ultrasound transducer 40 is excited, second ultrasound waves 80 may be created in fluids 78 within the patient's body near the second ultrasound transducer 40 and may propagate to the second end 74 of the large area of interest 66.

When the first ultrasound waves 76 and the second ultrasound waves 80 both reach the first end 72 and the second end 74, respectively, of the large area of interest 66, the first ultrasound waves 76 and the second ultrasound waves 80 may cause the large area of interest 66 to begin to vibrate. When the large area of interest 66 vibrates, the large area of interest 66 may start to become therapeutically heated to relieve pain or become stimulated or relaxed. If the large area of interest 66 is undesired, however, the first ultrasound transducer 38 and the second ultrasound transducer 40 may disintegrate the large area of interest 66. To disintegrate the large area of interest 66, the first ultrasound transducer 38 and the second ultrasound transducer 40 may transmit the first ultrasound waves 76 and the second ultrasound waves 80, respectively, with a fundamental harmonic (not shown) substantially equal to a resonant frequency (not shown) of the large area of interest 66. The control system 12 may continue to excite both the first ultrasound transducer 38 and the second ultrasound transducer 40 until the therapy has been completed.

Figure 7:
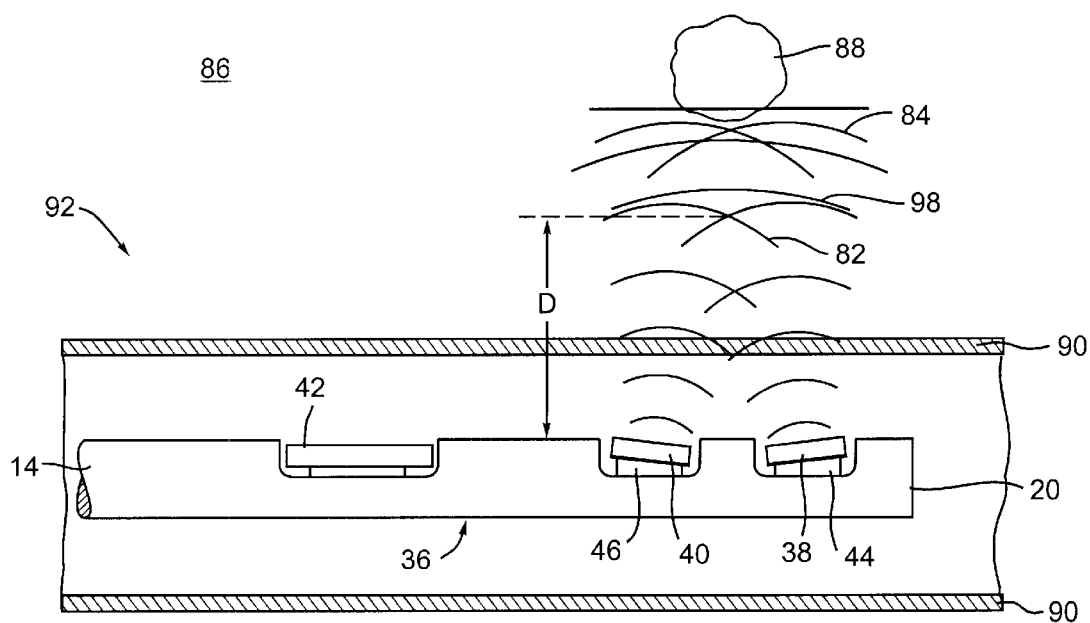
FIG. 7 is an illustration of a third preferred embodiment of a catheter in accordance with the present invention when operated in a transmitting mode.
Figure 8:
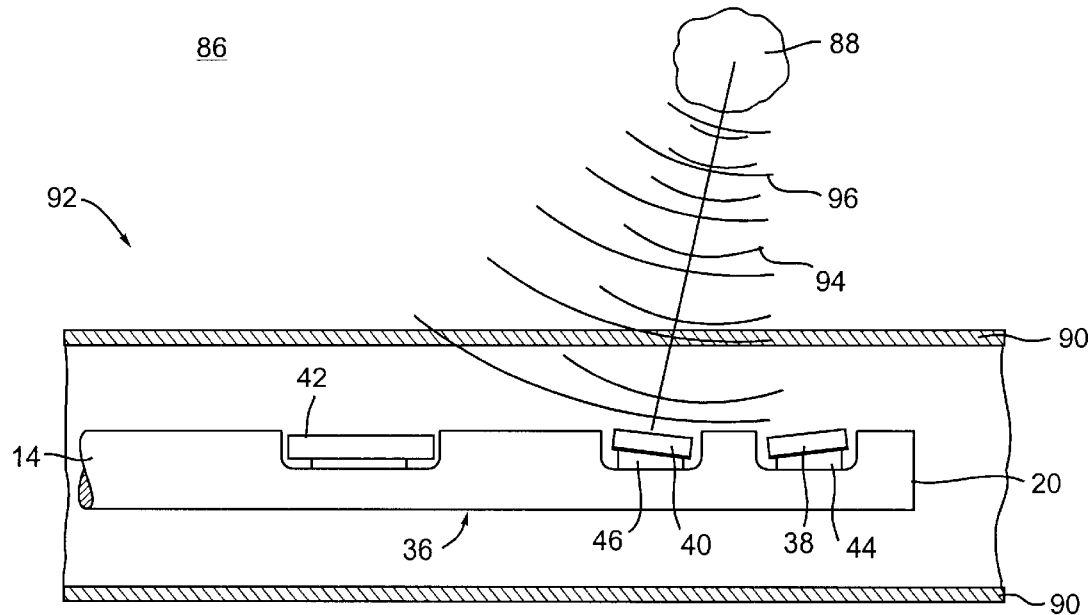
FIG. 8 is a detailed view of the catheter of FIG. 7 when operated in a receiving mode.

A third preferred embodiment of the catheter 36 of the present invention is shown in FIG. 7. The catheter 36 in the third embodiment preferably comprises a second ultrasound transducer 40 for transmitting and receiving ultrasound waves. The second ultrasound transducer 40 preferably has a preselected center frequency (not shown) that differs from the center frequency of the first ultrasound transducer 38. The first ultrasound transducer 38 and the second ultrasound transducer 40 may be directed such that ultrasound waves 84 generated by the first ultrasound transducer 38 preferably converge with ultrasound waves 82 created by the second ultrasound transducer 40, creating difference ultrasound waves 98.

The third ultrasound transducer 42 preferably has a center frequency (not shown) substantially equal to a difference between the fundamental harmonic of the ultrasound waves 84 generated by the first ultrasound transducer 38 and a fundamental harmonic (not shown) of the ultrasound waves 82 produced by the second ultrasound transducer 40. The ultrasound waves 82 of the second ultrasound transducer, and the difference ultrasound waves 98 each may be reflected by an area of interest 88 and, thereafter, received by the second ultrasound transducer 40 and the third ultrasound transducer 38, respectively.

In operation, the catheter 36 may be coupled to a control system 12 (shown in FIG. 1) for providing diagnostic scans from within, for example, a blood vessel 90 near a remote region 86 of a patient's body (not shown). The control system 12 may direct both the first ultrasound transducer 38 and the second ultrasound transducer 40 toward an area of interest 88 in the remote region 86 by moving the catheter 36 within the blood vessel 68 and/or by activating either the first steering device 44, the second steering device 46, or both. The first ultrasound transducer 38 and the second ultrasound transducer 40 may be directed such that the ultrasound waves 84 of the first ultrasound transducer 38 and the ultrasound waves 82 of the second ultrasound transducer 40 substantially converge at a distance D from the catheter 36. The distance D may be substantially equal to or less than a distance between the catheter 36 and the area of interest 88, and may be controlled by activating either the first steering device 44, the second steering device 46, or both.

The control system 12 may excite the first ultrasound transducer 38 and the second ultrasound transducer 40 either by applying signals (not shown) with a fixed frequency or signals (not shown) sweeping through a range of frequencies. The control system may apply the signals with the fixed frequencies to both the first ultrasound transducer 38 and the second ultrasound transducer 40. For example, if the center frequency of the first ultrasound transducer 38 is 35.100

MHz and the center frequency of the second ultrasound transducer 40 equals 35.000 MHz, then the fundamental harmonic of the ultrasound waves 84 created by the first ultrasound transducer 38 may be substantially equal to 35.100 MHz, the fundamental harmonic of the ultrasound waves 82 produced by the second ultrasound transducer 40 may be substantially equal to 35.000 MHz, and the center frequency of the third ultrasound transducer 42 preferably is substantially equal to the difference, 100 KHz. Alternatively, the first ultrasound transducer 38 and the second ultrasound transducer 40 may be excited by the signals that sweep through the range of frequencies. As the control system sweeps the first ultrasound transducer 38 and the second ultrasound transducer 40 each through the range of frequencies, a difference between a fundamental harmonic of the ultrasound waves transmitted by the first ultrasound transducer 38 and a fundamental harmonic of the ultrasound waves generated by the second ultrasound transducer 40 preferably remains substantially constant. Very preferably, the difference between the fundamental harmonic of the ultrasound waves transmitted by the first ultrasound transducer 38 and the fundamental harmonic of the ultrasound waves generated by the second ultrasound transducer 40 is substantially equal to 100 KHz.

When excited, the first ultrasound transducer 38 and the second ultrasound transducer 40 preferably produce the ultrasound waves 84 and the ultrasound waves 82, respectively, in fluids 92 within the patient's body surrounding the catheter 36. The ultrasound waves 84 from the first ultrasound transducer 38 and the ultrasound waves 82 from the second ultrasound transducer 40 may propagate through the fluids 92 of the patient's body toward the area of interest 88. Difference ultrasound waves 98 may result when the ultrasound waves 84 of the first ultrasound transducer 38 and the ultrasound waves 82 of the second ultrasound transducer 40 converge. The difference ultrasound waves 98 preferably have a fundamental harmonic (not shown) that is substantially equal to a difference between a fundamental harmonic (not shown) of the ultrasound waves 84 of the first ultrasound transducer 38 and a fundamental harmonic (not shown) of the ultrasound waves 82 of the second ultrasound transducer 40.

The ultrasound waves 82 from the second ultrasound transducer 40 and the difference ultrasound waves 98 each may reach the area of interest 88, and reflected fundamental ultrasound waves 94 and reflected difference ultrasound waves 96 may be formed, as shown in FIG. 7. The reflected fundamental ultrasound waves 94 may have a fundamental harmonic (not shown) that is substantially equal to the fundamental harmonic of the ultrasound waves 82 generated by the second ultrasound transducer 40, and the reflected difference ultrasound waves 96 preferably have a fundamental harmonic (not shown) substantially equal to the fundamental harmonic of the difference ultrasound waves 98. The reflected fundamental ultrasound waves 94 and the reflected difference ultrasound waves 96 each may return through the fluids 92 within the patient's body to the catheter 36.

Since the second ultrasound transducer 40 preferably has a center frequency substantially equal to the fundamental harmonic of the reflected fundamental ultrasound waves 94, the second ultrasound transducer 40 may be excited by the reflected ultrasound waves 94, creating electrical signals (not shown). The reflected difference ultrasound waves 96 may induce electrical signals (not shown) within the third ultrasound transducer 42 because the third ultrasound transducer 42 may have a center frequency substantially equal to the fundamental harmonic of the difference ultrasound waves 98. The control system 12 then may sense and process the induced electrical signals induced in both the second ultrasound transducer 40 and the third ultrasound transducer 42 to develop a diagnostic scan (not shown) and display a complete image (not shown) of the diagnostic scan. The complete image therefore may more accurately represent the area of interest 88 because the control system 12 may utilize information from both the reflected fundamental ultrasound waves 94 and the reflected difference ultrasound waves 96. Further, since the difference ultrasound waves 98 and the reflected difference ultrasound waves 96 are lower in frequency than either the ultrasound waves 84 of the first ultrasound transducer 38 or the ultrasound waves 82 of the second ultrasound transducer 40, the difference ultrasound waves 98 and the reflected difference ultrasound waves 96 may be less subject to attenuation during propagation through the patient's body. Thus, the difference ultrasound waves 98 and the reflected difference ultrasound waves 96 also may be able to travel deeper into the patent's body, providing diagnostic scans of the areas of interest 88 otherwise beyond a practical range of the first ultrasound transducer 38 and the second ultrasound transducer 40.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

For example, the first ultrasound transducer 38 may be disposed between the second ultrasound transducer 40 and the third ultrasound transducer 42, or the third ultrasound transducer 42 may be located between the first ultrasound transducer 38 and the second ultrasound transducer 40. In addition, the distance $d_1$, as shown in FIG. 3, between the first ultrasound transducer 38 and the second ultrasound transducer 40 may be greater than or less than the distance $d_2$ between the first ultrasound transducer 38 and the third ultrasound transducer 42.

The first ultrasound transducer 38 alternatively may be substantially concave in shape for reducing a focal length (not shown) of the first ultrasound transducer 38 or may be substantially convex in shape for increasing the focal length of the first ultrasound transducer 38. The second ultrasound transducer 40 of the second embodiment may also be substantially concave or convex in shape to increase or reduce, respectively, a focal length of the second ultrasound transducer 40. Finally, the first ultrasound transducer 38, and the second ultrasound transducer 40 each may include a backing layer 48 and a backing layer 60, respectively, as shown in FIG. 3. The backing layer 48 may be attached to a back surface 50 of the first ultrasound transducer 38 to absorb any energy radiating from the back surface 50 of the first ultrasound transducer 38. Similarly, any energy radiating from the back surface 62 of the second ultrasound transducer 40 may be absorbed by the backing layer 60 that may be attached to a back surface 62 of the second ultrasound transducer 40. The backing layer 48 and the backing layer 60 each preferably are formed from a high impedance material and act to minimize image distortion resulting from reflections of undesired signals.

What is claimed is:

1. A medical device for a medical imaging system, the medical device comprising:

an elongate body adapted to be inserted into a patient's body;

a drive shaft being substantially within the elongate body and having a proximal end portion and a distal end portion, the proximal end portion adapted to communicate with the medical imaging system;

a first imaging device adapted to transmit energy and has a center frequency, the first imaging device being mounted on or near the distal end portion of the drive shaft;

a second imaging device adapted to receive a reflection of the energy transmitted by the first imaging device, the second imaging device being mounted on or near the distal end portion of the drive shaft at a distance from the first imaging device and having a center frequency substantially equal to a fundamental harmonic of the energy transmitted by the first imaging device; and a third imaging device adapted to receive a reflection of the energy transmitted by the first imaging device, the third imaging device being mounted on or near the distal end portion of the drive shaft at a distance from the first imaging device and having a center frequency substantially equal to a second harmonic of the energy transmitted by the first imaging device.

2. The medical device of claim 1, wherein the proximal end portion of the drive shaft rotatably communicates with the medical imaging system.

3. The medical device of claim 1, wherein the preselected distance between the first imaging device and the second imaging device is less than the preselected distance between the first imaging device and the third imaging device.

4. The medical device of claim 1, wherein the second imaging device is disposed between the first imaging device and the third imaging device.

5. The medical device of claim 1, wherein the first imaging device is fixedly mounted on the distal end portion of the drive shaft.

6. The medical device of claim 1, wherein the first imaging device is adjustably mounted on the distal end portion of the drive shaft.

7. The medical device of claim 6, wherein the first imaging device has a first steering device.

8. The medical device of claim 7, wherein the first steering device comprises a piezoelectric steering device.

9. The medical device of claim 7, wherein the first steering device comprises an electric-field steering device.

10. The medical device of claim 1, wherein the second imaging device is fixedly mounted on the distal end portion of the drive shaft.

11. The medical device of claim 1, wherein the second imaging device is adjustably mounted on the distal end portion of the drive shaft.

12. The medical device of claim 11, wherein the second imaging device has a second steering device.

13. The medical device of claim 12, wherein the second steering device comprises a piezoelectric steering device.

14. The medical device of claim 12, wherein the second steering device comprises an electric-field steering device.

15. The medical device of claim 1, wherein the third imaging device is fixedly mounted on the distal end portion of the drive shaft.

16. The medical device of claim 1, wherein the first imaging device, the second imaging device, and the third imaging device each have a substantially uniform thickness.

17. The medical device of claim 1 wherein the first imaging device comprises an ultrasound transducer adapted to transmit the energy in the form of ultrasound waves.

18. The medical device of claim 17 wherein the second imaging device comprises an ultrasound transducer adapted to receive the reflection of the energy in the form of ultrasound waves.

19. The medical device of claim 18 wherein the third imaging device comprises an ultrasound transducer adapted to receive the reflection of the energy in the form of ultrasound waves.

20. The medical device of claim 17, further comprising a backing layer for absorbing energy radiating from a back surface of the first imaging device, the backing layer coupled to the back surface of the first imaging device.

21. The medical device of claim 20, wherein the backing layer is formed from a high impedance material.

22. The medical device of claim 1, wherein the first imaging device is substantially flat.

23. The medical device of claim 1, wherein the first imaging device is substantially concave.

24. The medical device of claim 1, wherein the first imaging device is substantially convex.

25. The medical device of claim 1, wherein the medical device is a catheter and the elongate body includes a catheter body.

26. A medical device for a medical imaging system, the medical device comprising:

an elongate body adapted to be inserted into a patient's body;

a drive shaft being substantially within the elongate body and having a proximal end portion and a distal end portion, the proximal end portion adapted to communicate with the medical imaging system;

a first imaging device adapted to transmit energy and has a center frequency, the first imaging device being mounted on or near the distal end portion of the drive shaft; and a second imaging device adapted to transmit energy, the second imaging device being mounted on or near the distal end portion of the drive shaft at a preselected distance from the first imaging device and having a center frequency substantially equal to the center frequency of the first imaging device.

27. The medical device of claim 26, wherein the energy transmitted by the first imaging device and the energy transmitted by the second imaging device substantially diverge.

28. The medical device of claim 27, wherein the first imaging device is directed toward a first end of a tissue segment, and wherein the second imaging device is directed toward a second end of the tissue segment.

29. The medical device of claim 26, wherein the proximal end portion of the drive shaft rotatably communicates with the medical imaging system.

30. The medical device of claim 26, wherein the first imaging device is fixedly mounted on the distal end portion of the drive shaft.

31. The medical device of claim 26, wherein the first imaging device is adjustably mounted on the distal end portion of the drive shaft.

32. The medical device of claim 31, wherein the first imaging device has a first steering device.

33. The medical device of claim 32, wherein the first steering device comprises a piezoelectric steering device.

34. The medical device of claim 32, wherein the first steering device comprises an electric-field steering device.

35. The medical device of claim 26, wherein the second imaging device is fixedly mounted on the distal end portion of the drive shaft.

36. The medical device of claim 26, wherein the second imaging device is adjustably mounted on the distal end portion of the drive shaft.

37. The medical device of claim 36, wherein the second imaging device has a second steering device.

38. The medical device of claim 37, wherein the second steering device comprises a piezoelectric steering device.

39. The medical device of claim 37, wherein the second steering device comprises an electric-field steering device.

40. The medical device of claim 26, wherein the first imaging device and the second imaging device each have a substantially uniform thickness.

41. The medical device of claim 26, wherein the first imaging device includes an ultrasound transducer adapted to transmit the energy in the form of ultrasound waves.

42. The medical device of claim 41, further comprising a backing layer for absorbing energy radiating from a back surface of the first imaging device, the backing layer coupled to the back surface of the first imaging device.

43. The medical device of claim 42, wherein the backing layer is formed from a high impedance material.

44. The medical device of claim 26, wherein the first imaging device is substantially flat.

45. The medical device of claim 26, wherein the first imaging device is substantially concave.

46. The medical device of claim 26, wherein the first imaging device is substantially convex.

47. The medical device of claim 41, wherein the second imaging device includes an ultrasound transducer adapted to transmit the energy in the form of ultrasound waves.

48. The medical device of claim 47, further comprising a backing layer for absorbing energy radiating from a back surface of the second imaging device, the backing layer coupled to the back surface of the second imaging device.

49. The medical device of claim 48, wherein the backing layer is formed from a high impedance material.

50. The medical device of claim 26, wherein the second imaging device is substantially flat.

51. The medical device of claim 26, wherein the second imaging device is substantially concave.

52. The medical device of claim 26, wherein the second imaging device is substantially convex.

53. The medical device of claim 26, wherein the medical device is a catheter and the elongate body includes a catheter body.

54. A medical device for a medical imaging system, the medical device comprising:
    a drive shaft having a proximal end portion and a distal end portion, the proximal end portion adapted to communicate with the medical imaging system;
    a first imaging device adapted to transmit energy and has a center frequency, the first imaging device being mounted on or near the distal end portion of the drive shaft; and
    a second imaging device adapted to transmit and receive energy, the second imaging device being mounted on or near the distal end portion of the drive shaft at a distance from the first imaging device and having a center frequency differing from the center frequency of the first imaging device, the energy transmitted by the second imaging device substantially converging with the energy transmitted by the first imaging device and forming a difference energy having a fundamental harmonic substantially equal to a difference between a fundamental harmonic of the energy transmitted by the first imaging device and a fundamental harmonic of the energy transmitted by the second imaging device.

55. The medical device of claim 54 further comprising a third imaging device adapted to receive energy, the third imaging device being mounted on or near the distal end portion of the drive shaft at a distance from the first imaging device and having a center frequency substantially equal to a difference between the fundamental harmonic of the energy transmitted by the first imaging device and the fundamental harmonic of the energy transmitted by the second imaging device, and being directed to receive a reflection of the difference energy.

56. The medical device of claim 54, wherein the proximal end portion of the drive shaft rotatably communicates with the medical imaging system.

57. The medical device of claim 54, wherein the distance between the first imaging device and the second imaging device is less than the distance between the first imaging device and the third imaging device.

58. The medical device of claim 54, wherein the second imaging device is disposed between the first imaging device and the third imaging device.

59. The medical device of claim 54, wherein the energy transmitted by the first imaging device and the energy transmitted by the second imaging device substantially converge at a preselected distance from the drive shaft.

60. The medical device of claim 59, wherein the first imaging device has a first steering device for controlling a distance from the drive shaft at which the energy transmitted by the first imaging device and the energy transmitted by the second imaging device substantially converge.

61. The medical device of claim 60, wherein the first steering device comprises a piezoelectric steering device.

62. The medical device of claim 60, wherein the first steering device comprises an electric-field steering device.

63. The medical device of claim 62, wherein the second imaging device has a second steering device for controlling a distance from the drive shaft at which the energy transmitted by the first imaging device and the energy transmitted by the second imaging device substantially converge.

64. The medical device of claim 63, wherein the second steering device comprises a piezoelectric steering device.

65. The medical device of claim 63, wherein the second steering device comprises an electric-field steering device.

66. The medical device of claim 55, wherein the first imaging device and the second imaging device each are excited by a signal having a fixed frequency.

67. The medical device of claim 66, wherein the frequency of the energy transmitted by the first imaging device is 35.100 MHz, the frequency of the energy transmitted and received by the second imaging device is 35.000 MHz, and the frequency of the energy received by the third imaging device is 100 KHz.

68. The medical device of claim 54, wherein the first imaging device and the second imaging device each are excited by a signal sweeping through a range of frequencies, a difference between a fundamental harmonic of the energy transmitted by the first imaging device and a fundamental harmonic of the energy transmitted by the second imaging device being substantially constant.

69. The medical device of claim 68, wherein the difference between the fundamental harmonic of the energy transmitted by the first imaging device and the fundamental harmonic of the energy transmitted by the second imaging device is substantially equal to 100 KHz.

70. A method of manufacturing a medical device for a medical imaging system, the method comprising:
    providing an elongate body and a drive shaft disposed at least partially in the elongate body, the drive shaft having a proximal end portion and a distal end portion, the proximal end portion adapted to communicate with the medical imaging system;

mounting a first imaging device adapted to transmit energy on or near the distal end portion of the drive shaft and having a center frequency;

mounting a second imaging device adapted to receive energy on or near the distal end portion of the drive shaft at a distance from the first imaging device and having a center frequency substantially equal to a fundamental harmonic of the energy transmitted by the first imaging device; and mounting a third imaging device adapted to receive energy on or near the distal end portion of the drive shaft at a distance from the first imaging device and having a center frequency substantially equal to a second harmonic of the energy transmitted by the first imaging device.

71. A method of manufacturing a medical device for a medical imaging system, the method comprising:

providing an elongate body and a drive shaft disposed at least partially in the elongate body, the drive shaft having a proximal end portion and a distal end portion, the proximal end portion adapted to communicate with the medical imaging system;

mounting a first imaging device adapted to transmit energy on or near the distal end of the drive shaft and having a center frequency; and mounting a second imaging device adapted to transmit energy on or near the distal end of the drive shaft at a distance from the first imaging device and having a center frequency substantially equal to the center frequency of the first imaging device.

72. A method of manufacturing a medical device for a medical imaging system, the method comprising:

providing an elongate body and a drive shaft disposed at least partially in the elongate body, the drive shaft having a proximal end portion and a distal end portion, the proximal end portion adapted to communicate with the medical imaging system;

mounting a first imaging device adapted to transmit energy on or near the distal end portion of the drive shaft and having a center frequency;

mounting a second imaging device adapted to transmit and receive energy on or near the distal end portion of the drive shaft at a distance from the first imaging device and having a center frequency differing from the center frequency of the center frequency of the first imaging device; and mounting a third imaging device adapted to receive energy on or near the distal end portion of the drive shaft at a distance from the first imaging device and having a center frequency substantially equal to a difference between a fundamental harmonic of the energy transmitted by the first imaging device and the a fundamental harmonic of the energy transmitted by the second imaging device.

* * * * *